US007351780B2

(12) United States Patent
Hope et al.

(10) Patent No.: US 7,351,780 B2
(45) Date of Patent: Apr. 1, 2008

(54) METHOD FOR MANUFACTURING HIGH VISCOSITY POLYALPHAOLEFINS USING IONIC LIQUID CATALYSTS

(75) Inventors: Kenneth D. Hope, Kingwood, TX (US); Donald A. Stern, Kingwood, TX (US); Donald W. Twomey, Kingwood, TX (US); J. Barry Collins, New Caney, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 235 days.

(21) Appl. No.: 10/420,261

(22) Filed: Apr. 22, 2003

(65) Prior Publication Data

US 2004/0030075 A1 Feb. 12, 2004

Related U.S. Application Data

(60) Provisional application No. 60/374,528, filed on Apr. 22, 2002.

(51) Int. Cl.
*C08F 4/52* (2006.01)
*C08F 4/14* (2006.01)

(52) U.S. Cl. ............... 526/217; 526/237; 526/348; 526/348.3; 525/338; 585/502

(58) Field of Classification Search ............. 585/502, 585/520, 527; 526/217, 237, 236, 348, 348.3; 525/338
See application file for complete search history.

(56) References Cited

U.S. PATENT DOCUMENTS

| 2,405,950 | A | | 8/1946 | Hanford | |
|---|---|---|---|---|---|
| 4,827,064 | A | | 5/1989 | Wu | 585/10 |
| 5,087,782 | A | | 2/1992 | Pelrine | 585/417 |
| 5,196,574 | A | | 3/1993 | Kocal | |
| 5,304,615 | A | | 4/1994 | Ambler | 526/189 |
| 5,386,072 | A | | 1/1995 | Cozzi et al. | |
| 5,573,657 | A | * | 11/1996 | Degnan et al. | 208/144 |
| 5,731,101 | A | * | 3/1998 | Sherif et al. | 429/102 |
| 5,824,832 | A | | 10/1998 | Sherif | 585/455 |
| 5,891,830 | A | | 4/1999 | Koltermann | 308/136 |
| 6,087,307 | A | | 7/2000 | Kaminski | 508/223 |
| 6,107,374 | A | * | 8/2000 | Stevens et al. | 524/60 |
| 6,284,937 | B1 | * | 9/2001 | Olivier et al. | 585/502 |
| 6,395,948 | B1 | * | 5/2002 | Hope et al. | 585/510 |
| 6,841,711 | B2 | * | 1/2005 | Krug et al. | 585/326 |
| 2001/0006154 | A1 | * | 7/2001 | Krug et al. | 208/18 |
| 2002/0128532 | A1 | | 9/2002 | Hope | 585/521 |
| 2003/0085156 | A1 | | 5/2003 | Schoonover | |
| 2004/0005985 | A1 | | 1/2004 | Hope et al. | |
| 2004/0030075 | A1 | | 2/2004 | Hope et al. | |

FOREIGN PATENT DOCUMENTS

| EP | 0791643 | | 8/1997 |
|---|---|---|---|
| EP | 791643 | * | 8/1997 |
| WO | WO 88/06576 A1 | | 9/1988 |
| WO | WO 95/21871 | | 8/1995 |
| WO | WO 95/21872 | | 8/1995 |
| WO | WO 98/50153 A1 | | 11/1998 |
| WO | WO 99/38938 | | 8/1999 |
| WO | WO 00/32658 A1 | | 6/2000 |
| WO | WO 00/41809 | | 7/2000 |
| WO | WO 01/64622 | | 9/2001 |
| WO | WO 03/089390 A2 | | 10/2003 |

OTHER PUBLICATIONS

Communication Relating to the Results of the Partial International Search, PCT/US 03/12821; Sep. 4, 2003; 3 pages.
Wasserscheid P. et al.; "Ionic Liquids—New Solutions for Transition Metal Catalysis"; Ange Chem. International Edition; vol. 39, Oct. 27, 2000; pp. 3772-3789.
International Search Report, PCT/US 03/12821, Jan. 29, 2004; 7 pages.
International Search Report and Written Opinion of the International Searching Authority, PCT/US2004/036188, Feb. 23, 2005, 9 pgs.
Schubert, H., "Mechanical Emulsification—New Developments and Trends," Aiche National Meeting, Nov. 12, 2000, XP001160577, 15 pgs.
International Search Report and Written Opinion of the International Searching Authority, PCT/US2004/036410, Feb. 21, 2005, 7 pgs.
Written Opinion of the International Preliminary Examining Authority, PCT/US 03/12821, Feb. 18, 2004, 6 pgs.
International Search Report, PCT/US 03/12823, Dec. 17, 2003, 5 pgs.
Written Opinion of the International Preliminary Examining Authority, PCT/US 03/12823, Jul. 26, 2003, 6 pgs.
International Search Report, PCT/US 03/04838, Jun. 12, 2003, 4 pgs.
Written Opinion of the International Preliminary Examining Authority, PCT/US 03/04838, Apr. 8, 2004, 6 pgs.
U.S. Appl. No. 10/900,221, filed Jul. 27, 2004, Specification and Drawings (Figures 1-5), 28 pgs.

* cited by examiner

*Primary Examiner*—Roberto Rabago
(74) *Attorney, Agent, or Firm*—Conley Rose, P.C.; Rodney B. Carroll

(57) ABSTRACT

A method of continuously manufacturing a high viscosity polyalphaolefin product by introducing a monomer and an ionic liquid catalyst together into a reaction zone while simultaneously withdrawing from the reaction zone a reaction zone effluent that contains the high viscosity polyalphaolefin. The reaction zone is operated under reaction conditions suitable for producing the high viscosity polyalphaolefin product. The preferred high viscosity polyalphaolefin has a kinematic viscosity exceeding about 8 cSt and is the reaction product of the trimerization, oligomerization, or polymerization of an alpha olefin or a mixture of one or more product thereof. The high viscosity polyalphaolefins are useful as lubricants or lubricant additives.

21 Claims, 2 Drawing Sheets

METHOD FOR MANUFACTURING HIGH VISCOSITY POLYALPHAOLEFINS USING IONIC LIQUID CATALYSTS

CROSS-REFERENCE TO RELATED APPLICATIONS

This application claims the benefit of and priority to provisional U.S. patent application No. 60/374,528, filed Apr. 22, 2002 and entitled "Method for Manufacturing High Viscosity Polyalphaoleflns Using Ionic Liquid Catalysts". This application is related to U.S. patent application Ser. No. 10/420,182 filed on Apr. 22, 2003, U.S. Pat. No. 6,984,605, and entitled "Method for Manufacturing Ionic Liquid Catalysts." Each of the above-listed applications is hereby incorporated herein by reference in its entirety for all purposes.

FIELD OF THE INVENTION

The present invention relates to a continuous process for the manufacture of high viscosity polyalphaolefin products from an alphaolefin feedstock using an ionic liquid catalyst where the polyalphaolefin products have unique physical properties that make them useful as lubricants or lubricant additives.

BACKGROUND

It is known that alpha olefins may be oligomerized to prepare synthetic oil base stocks, but many of these oligomerization products do not have the physical properties desired for certain applications, and they are often expensive to manufacture.

U.S. Pat. No. 5,304,615 discloses a process for the polymerization of butene using an ionic liquid as a catalyst, but the disclosure does not suggest a continuous process or the use of an ionic liquid composition derived from the combination of an alky-containing amine hydrohalide salt and a metal halide.

U.S. Pat. No. 5,731,101 discusses the possible use of low temperature ionic liquids as a catalyst for dimerization, oligomerization, and polymerization, but it does not specifically teach the oligomerization or polymerization of alpha olefins; and, moreover, there is no suggestion of a continuous process using an ionic liquid to make polyalphaolefin products that are useful as lubricants or lubricant additives.

U.S. Pat. No. 5,824,832 is a continuation-in-part of U.S. Pat. No. 5,731,101 discussed above, and it focuses on the use of ionic liquids in the alkylation of aromatic molecules. The only exemplified reactions are those involving an aromatic compound, such as benzene and toluene. There is no suggestion of a continuous process using an ionic liquid to make a polyalphaolefin product.

EP 0791643 discloses a process for making lubricating oils by oligomerization of alpha olefins in the presence of an ionic liquid, but it does not teach the use of an ionic liquid composition derived from the combination of an alkyl-containing amine hydrohalide salt and a metal halide nor does it teach a continuous process.

Considering the above discussed prior art, it is clear that there is a need for an economical process that utilizes the advantages of continuous processing for the manufacture of a polyalphaolefin product having certain desirable physical properties.

SUMMARY OF THE INVENTION

It is, thus, an object of the invention to provide a continuous process for the manufacture of polyalphaolefins.

It is a further object of the invention for the process thereof to produce a polyalphaolefin product having physical properties which make it either a desirable lubricant or lubricant additive for certain applications.

A still further object is for the inventive continuous process to use certain ionic liquid catalysts that give polyalphaolefin product having unique properties making them especially useful in certain lubricant or lubricant additive applications.

The invention relates to a process for manufacturing a polyalphaolefin product that is useful as either a lubricant or lubricant additive. The polyalphaolefin product is made by a continuous process that includes the steps of introducing a monomer feed, comprising an alphaolefin, and a catalyst feed, comprising an ionic liquid catalyst, into a reaction zone while simultaneously withdrawing from the reaction zone a reaction effluent comprising the polyalphaolefin product.

Another embodiment of the invention relates to a method of controlling the viscosity of a polyalphaolefin product resulting from the ionic liquid catalyzed oligomerization of an alpha olefin by determining a correlation between the viscosity of the polyalphaolefin product and the concentration of the ionic liquid catalyst used in the oligomerization reaction. The correlation is used to set the concentration of the ionic liquid catalyst used in the reaction so as to provide the polyalphaolefin product having desired viscosity characteristics.

Still another embodiment of the invention relates to a novel polyalphaolefin composition produced by the ionic liquid catalyzed oligomerization of an alpha olefin to give such polyalphaolefin composition having unique physical properties.

DETAILED DESCRIPTION

Figure 1:
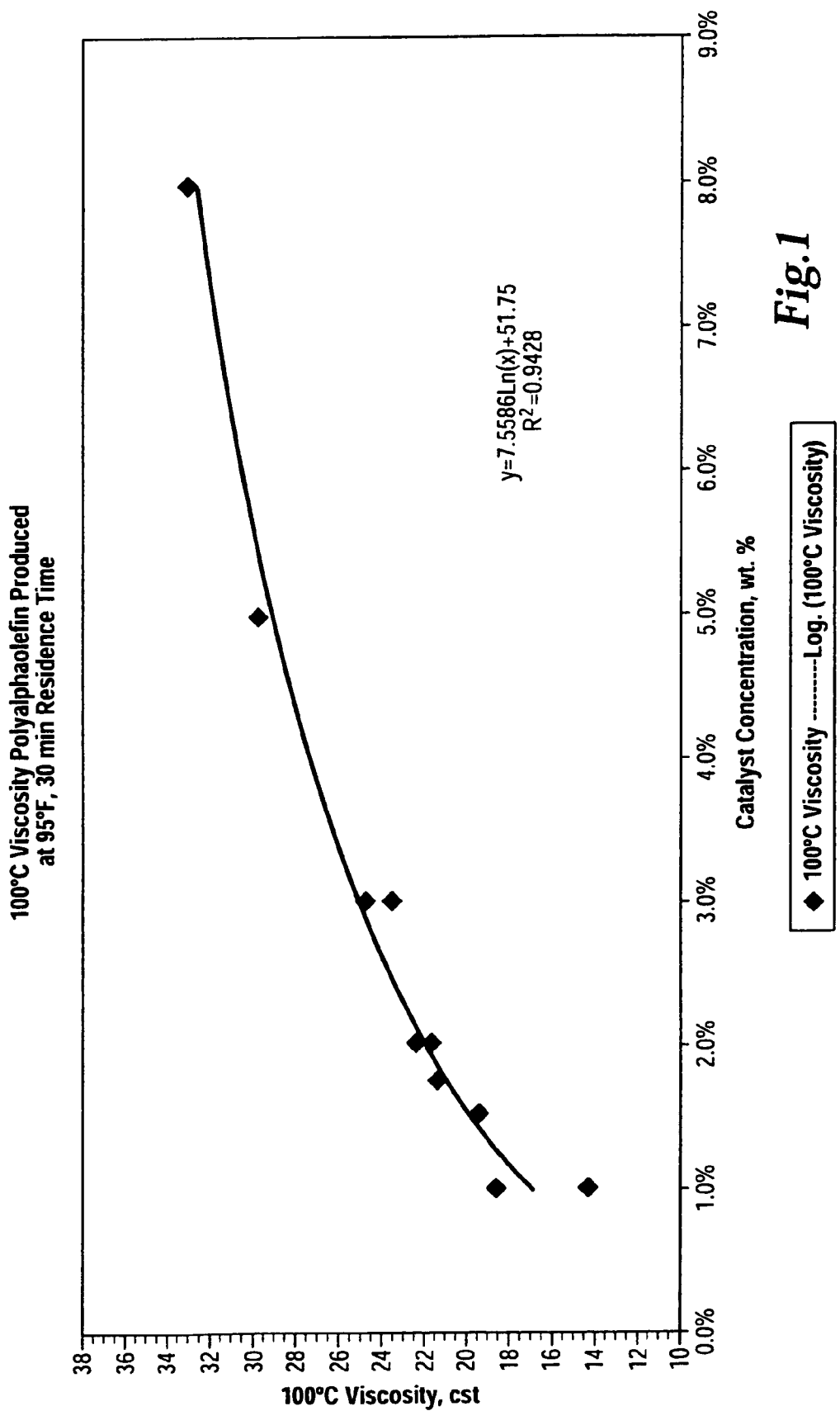
FIG. 1 is a plot of experimental data showing the correlation between the kinematic viscosity at 100° C. of an alpha olefin product produced from a continuous process for oligomerizing an alpha olefin monomer using an ionic liquid catalyst (aluminum trichloride trimethylamine hydrochloride) and the catalyst concentration as a percent, based on weight, of the monomer feedstock.

The inventive processes disclosed herein for manufacturing a high viscosity polyalphaolefin product are unique in that they are continuous processes. Further embodiments of the inventive processes include methods involving the adjustment of certain process variables to provide for the control of the physical properties of the high viscosity polyalphaolefin product to give a polyalphaolefin product having desired properties. One embodiment of the inventive process includes the introduction of both a monomer feed that comprises at least one alphaolefin and an ionic liquid catalyst into a reaction zone and withdrawing from said reaction zone during the introduction of the monomer feed and ionic liquid catalyst into said reaction zone a reaction effluent that comprises a polyalphaolefin product.

As used herein, the term "polyalphaolefin product" refers to a novel alpha olefin oligomerization product that is either a dimer, a trimer, a tetramer, higher oligomers, a polymer of an alpha olefin, or a mixture of any one or more thereof, each of which preferably has certain desired physical properties and, in particular, having the desired high viscosity properties all of which are more fully described below. The polyalphaolefin product may undergo subsequent processing such as hydrogenation to form a more stable product, for example useful as a base oil stock.

The reaction zone of the process can be defined by any reaction means known in the art that provides for the contacting of the monomer feed with the ionic liquid under suitable reaction conditions maintained and controlled so as to provide for the reaction of the monomer feed to thereby give the polyalphaolefin product. The reaction zone is generally defined by a reactor vessel into which the monomer feed and ionic liquid catalyst are introduced. The monomer feed and ionic liquid catalyst can be introduced separately into the reaction zone as separate feed streams, or they can be introduced together as a premixed mixture; but, because the monomer feed and ionic liquid catalyst are generally immiscible fluids, it is preferred for the reactor to be equipped with a mixing or stirring means for mixing the monomer feed and ionic liquid catalyst to provide the desired intimate contact of the two fluids or to provide the preferred substantially homogenous mixture of monomer feed and ionic liquid catalyst. One type of reactor that suitably provides for the required mixing of the monomer feed and ionic liquid catalyst is known in the art as a continuous stirred tank reactor (CSTR).

The reaction conditions within the reaction zone are maintained so as to provide suitable reaction conditions for the dimerization, oligomerization or polymerization or any combination thereof of the alphaolefin of the monomer feed to give a polyalphaolefin product. The reaction pressure generally can be maintained in the range of from below atmospheric upwardly to about 250 psia. Since the reaction is not significantly pressure dependent, it is most economical to operate the reactor at a low pressure, preferably, from about atmospheric to about 50 psia and, most preferably, from atmospheric to 25 psia. The reaction temperature is to be maintained during the reaction so as to keep the reactants and catalyst in the liquid phase. Thus, generally, the reaction temperature range is from about 20° F. to about 200° F. Preferably, the reaction temperature shall be in the range of from about 40° F. to about 150° F., and, most preferably, from 50° F. to 110° F.

The residence time of the feed within the reaction zone has a small influence on the resultant reaction product. As used herein, the term "residence time" is defined as being the ratio of the reactor volume to the volumetric introduction rate of the feeds, both the monomer feed and the ionic liquid catalyst feed, charged to or introduced into the reaction zone defined by a reactor. The residence time is in units of time. The reactor volume and feed introduction rate are such that the residence time of the total of the monomer feed and ionic liquid catalyst feed is generally in the range upwardly to about 300 minutes, but due to the need to have sufficient residence time for the reaction to take place and to economic considerations, the residence time is more appropriately in the range of from about 1 minute to about 200 minutes. Preferably, the residence time is in the range of from about 2 minutes to about 120 minutes and, more preferably, from 5 minutes to 60 minutes.

The amount of water present in the reaction zone may be controlled to maintain the reaction and avoid deactivating the ionic liquid catalyst. In an embodiment, the amount of water present in the reaction zone is from about 10 to about 20 ppm based upon the weight of the total reactants within the reaction zone. In an embodiment, the amount of water present in the reaction zone is controlled such that the amount is less than an upper amount that is sufficient to deactivate the ionic liquid catalyst (e.g., formation of an undesirable amount of aluminum hydroxide from aluminum trichloride) and greater than a lower amount that is insufficient to maintain the desired reaction (e.g., conversion of monomer feed to less than about 20 weight percent) in the reaction zone.

The lower amount of water for a given ionic liquid catalyst composition may be determined experimentally by iteratively reducing the amount of water in the reaction zone and monitoring the monomer conversion until such conversion is unacceptable for the desired reaction. Conversely, the upper amount of water for a given ionic liquid catalyst composition may be determined experimentally by iteratively increasing the amount of water in the reaction zone and monitoring the catalyst deactivation until such deactivation is unacceptable for the desired reaction. What constitutes acceptable ionic liquid catalyst activity may depend upon, for example, the specific catalyst composition, the reaction conditions, and/or the types and properties (such as viscosity targets) for the end products being made.

In some embodiments, the maximum upper amount of water is the stoichiometric ratio of water that reacts with the catalyst to create a non-catalytic species thereof. For an ionic liquid catalyst comprising aluminum trichloride that deactivates by reacting with water to form aluminum hydroxide, the maximum upper amount of water is a molar ratio of about 6 moles of water to each mole of aluminum trichloride.

The amount of water present in the reaction zone may be controlled by controlling the amount of water in the monomer feed to the reaction zone, controlling the amount of water in a gas located in a head space above the liquid components present in the reaction zone, or combinations thereof. The amount of water present in the ionic liquid catalyst, if any, is typically about constant and thus is not routinely adjusted or changed after initial control calibrations are performed.

In an embodiment where the amount of water present in the monomer feed is controlled, the amount of water present in the feed is from about 5 to about 15 ppm based upon the weight of the monomer feed. In an embodiment where the amount of water present in a head space gas is controlled, the monomer feed is dried to a water content of less than about 1 ppm by weight and an amount of oxygen or wet gas such as moist nitrogen is added to the reaction zone to control the amount of water therein. The moist nitrogen may be produced, for example, by bubbling dry nitrogen through water. The oxygen may be pure oxygen, air, dried air, oxygen enriched air, other oxygen sources such as a process stream, or combinations thereof, and the stream of oxygen, for example dried air, may have less than about 1 ppm of water by weight therein.

In an embodiment where the monomer feed is dried to less than about 1 ppm by weight and the head space gas is dry nitrogen, the amount of water present in the reaction zone may be insufficient to maintain the desired reaction in the reaction zone, that is the conversion of the monomer feed was less than about 20 weight percent. In such an embodiment, the weight percent conversion of monomer feed can be increased by increasing the amount of water present in the reaction zone as discussed previously, for example by adding air or moist nitrogen to the reaction zone head space or by other methods as known to those skilled in the art. Stated alternatively, an amount of water can be added to the ionic liquid catalyst in a manner described previously to activate the catalyst and thereby increase the weight percent conversion of monomer feed, provided however that such amount of added water is less than an amount that undesirably deactivates the catalyst.

Without intending to be bound by theory, it is believed that the ionic liquid catalysts require the presence of a proton donor such as an acid, and that water present or formed in the reaction zone reacts with the catalyst (e.g., aluminum trichloride) to form hydrogen chloride, which serves as a proton donor to the remaining catalyst. In an embodiment, an acid, for example hydrogen chloride or other acids such a Bronsted acid or a Lewis acid, is added directly to the ionic liquid catalyst. For example, hydrogen chloride may be added directly to the ionic liquid catalyst by bubbling hydrogen chloride gas through the ionic liquid catalyst or by any other methods as known to those skilled in the art.

The rate of introduction of ionic liquid catalyst into the reaction zone relative to the rate of introduction of monomer feed is an important feature of the inventive continuous process in that the control of the catalyst concentration can be used to control certain of the physical properties of the polyalphaolefin product. Thus, in one embodiment of the inventive process the weight ratio of ionic liquid catalyst to monomer feed is set so as to provide a polyalphaolefin product having desired physical properties. Generally, the weight ratio of ionic liquid catalyst to monomer feed is in the range upwardly to about 1:1, but it should more normally be in the range from about 0.01:100 to about 25:100. Preferably, the weight ratio of ionic liquid catalyst to monomer feed introduced into the reaction zone of the process is in the range of from 0.1:100 to 20:100 and, more preferably, in the range of from 0.1:100 to 15:100.

The monomer feedstock that is introduced into the reaction zone of the process comprises at least one alpha olefin hydrocarbon. Preferably, the monomer feed is substantially all alpha olefin, thus providing a concentration of alpha olefin in the monomer feed of at least about 50 weight percent, based on the monomer feed. It is best, however, for the concentration of alpha olefin in the monomer feed to be at least 75 weight percent, preferably, at least 95 weight percent, and most preferably, at least 99 weight percent. The alpha olefins, which are also known as 1-olefins or 1-alkenes, suitable for use as the monomer feed of the process can have from 4 to 20 carbon atoms and include, for example, 1-butene, 1-pentene, 1-hexene, 1-octene, 1-decene, 1-dodecene, and 1-tetradecene. It is preferred for the alpha olefin of the monomer feed to be those having from 4 to 14 carbon atoms. It is noted that the alpha olefins of 1-decene and 1-dodecene provide for a polyalphaolefin product resulting from the inventive process described herein that have especially desirable physical properties.

The reactor effluent withdrawn from the reaction zone of the inventive process generally can comprise the polyalphaolefin product of the process and the ionic liquid catalyst. The reactor effluent can further comprise a dimer of the alpha olefin in the monomer feed and the unreacted monomer, if any. The polyalphaolefin product can be separated from the other components of the reactor effluent including the ionic liquid catalyst, and, optionally, the unreacted monomer and dimers formed during the reaction of the monomer feed. The separated polyalphaolefin product may further be processed by methods such as hydrogenation to impart other desired properties. The polyalphaolefin product can include dimers, trimers, tetramers, higher oligomers, polymers, or mixture of any one or more thereof of the alpha olefin contained in the monomer feed. Such dimers, trimers, tetramers, higher oligomers, polymers, or mixture of any one or more thereof may comprise molecules having from 12 to over 1300 carbon atoms.

A particularly preferred polyalphaolefin product of the process is that manufactured, using the inventive process, from either a 1-decene or 1-dodecene feedstock. The polyalphaolefin products from these feedstocks are especially significant in that they have unique physical properties. Typical ranges for the various physical properties of the polyalphaolefin product and the relevant test methods for determining the physical properties are presented in the following Table of "Product Physical Properties."

| Test | Units | Test Method | | Value |
|---|---|---|---|---|
| Kinematic Viscosity at 100° C. | cSt | ASTM D445 | Min | 12.0 |
| | | | Max | 35.0 |
| Bromine Index | mg/100 g | ASTM D2710 | Max | 800 |
| Volatility, Noack | wt % | CEC L40 T87 | Max | 2.0 |
| Flash Point | ° C. | ASTM D92 | Min | 245 |
| Fire Point | ° C. | ASTM D92 | Min | 290 |
| Pour Point | ° C. | ASTM D97 | Max | −30 |
| Polydispersity Index | | | Max | 3.5 |
| | | | Min | 1.0 |
| Weight Average Molecular Weight | | | Min | 170 |
| | | | Max | 18200 |

Presented in FIG. 1 is an exemplary plot showing the correlation between the kinematic viscosity at 100° C. of the alpha olefin product produced from a continuous process for oligomerizing an alpha olefin monomer using an ionic liquid catalyst (aluminum trichloride trimethylamine hydrochloride) and the ionic liquid catalyst concentration. The correlation is believed to be unexpected and can be used in the control of the kinematic viscosity of an alpha olefin end-product produced by the ionic liquid catalyzed oligomerization of alpha olefin. A determination is first made of the correlation between the weight ratio of ionic liquid catalyst to monomer feed and the kinematic viscosity of the polyalphaolefin product resulting from the oligomerization reaction. This correlation is then utilized to determine the concentration of ionic liquid catalyst necessary for providing the polyalphaolefin product having desired viscosity properties.

Generally, the kinematic viscosity at 100° C. of the polyalphaolefin product exceeds about 8 cSt, but it is desirable for the kinematic viscosity at 100° C. to exceed about 12 cSt. Preferably, the kinematic viscosity of the polyalphaolefin product exceeds about 15 cSt, and most preferably, it exceeds 18 cSt. The desirable range for kinematic viscosity at 100° C. of the polyalphaolefin product is thus from about 8 cSt to about 40 cSt. Preferably, the range for kinematic viscosity at 100° C. of the polyalphaolefin product is from about 12 cSt to about 35 cSt and, most preferably, from 15 cSt to 30 cSt.

A particularly unique feature of the inventive polyalphaolefin product is that it has a low polydispersity index while having a high viscosity. It is desirable for the polydispersity index of the polyalphaolefin product to be as close to one as is possible; since, it is desirable for the polyalphaolefin product to have a narrow range of molecular weight. As used herein, the term polydispersity index refers to the ratio of weight average molecular weight ($M_w$) to number average molecular weight ($M_n$). The polydispersity index is an indication of the breath of the molecular weight range with a value of one for the polydispersity index indicating that all the molecules in the polyalphaolefin product have the same molecular weight.

The polydispersity index of the polyalphaolefin product should thus be in the range of from 1.0 to about 3.5 when the polyalphaolefin product has a high kinematic viscosity at 100° C. exceeding about 8 cSt. It is preferred for the polydispersity index of the polyalphaolefin product to be less than about 3.0 and, therefore, in the range of from 1.0 to about 3.0, when the kinematic viscosity at 100° C. exceeds about 12 cSt, preferably exceeding about 15 cSt, and most preferably exceeding 18 cSt. It is most preferred for the polydispersity index of the polyalphaolefin product to be in the range of from 1 to 2.5 when the polyalphaolefin product has a high kinematic viscosity at 100° C. so that it exceeds about 12 cSt, preferably 15 cSt, and most preferably 18 cSt.

As described above, the polydispersity index is defined as the ratio of the weight average molecular weight to number average molecular weight both of the polyalphaolefin product. The weight average molecular weight has a meaning understood by those skilled in the art to be the summation of the weight fraction of each molecular species times its molecular weight. The number average molecular weight is understood to medan the summation of the mole fraction of each molecular species times its molecular weight.

The weight average molecular weight of the inventive polyalphaolefin product can be in the range of from about 170 to about 18,200, but, more particularly, the range is from about 200 to about 10,000. Preferably, the weight average-molecular weight of the polyalphaolefin product that has a low polydispersity index while having a high viscosity is between 210 and 8,000 and, most preferably, the weight average molecular weight of the polyalphaolefin product is in the range of from 250 to 3,000.

Ionic liquid compositions suitable for use in the inventive process are complexes of two components that form compositions that are liquid under the reaction conditions of the inventive process. Specifically, the ionic liquid catalyst is the complex resulting from the combination of a metal halide and an alkyl-containing amine hydrohalide salt. Such compositions are described in detail in U.S. Pat. No. 5,731,101, the disclosure of which is incorporated herein by reference. It has been found that the use of such ionic liquid compositions provide for a polyalphaolefin end-products having certain desirable and novel physical properties that make them especially useful in various lubricant or lubricant additive applications.

The metal halides that can be used to form the ionic liquid catalyst used in this invention are those compounds which can form ionic liquid complexes that are in liquid form at the reaction temperatures noted above when combined with an alkyl-containing amine hydrohalide salt. Preferred metal halides are covalently bonded metal halides. Possible suitable metals which can be selected for use herein include those from Groups VIII, IB, IIB, and IIIA of the Periodic Table of the Elements, CAS version. More specifically, the metal of the metal halides can be selected from the group consisting of aluminum, gallium, iron, copper, zinc, and indium. Preferred among these metals are aluminum and gallium, and most preferred is aluminum. Preferred metal halides include those selected from the group consisting of aluminum halide, alkyl aluminum halide, gallium halide, and alkyl gallium halide, of which, especially preferred are aluminum halide or alkyl aluminum halide. The most preferred metal halide as a reactant for use in the inventive process is aluminum trichloride.

The alkyl-containing amine hydrohalide salts that can be used to form the ionic liquid catalyst used in this invention include monoamines, diamines, triamines and cyclic amines, all of which include one or more alkyl group and a hydrohalide anion. The term alkyl is intended to cover straight and branched alkyl groups having from 1 to 9 carbon atoms. The preferred alkyl-containing amine hydrohalide salts useful in this invention have at least one alkyl substituent and can contain as many as three alkyl substituents. They are distinguishable from quaternary ammonium salts which have all four of their substituent positions occupied by hydrocarbyl groups. The preferred compounds that are contemplated herein have the generic formula $R_3N \cdot HX$, where at least one of the "R" groups is alkyl, preferably an alkyl of from one to eight carbon atoms (preferably, lower alkyl of from one to four carbon atoms) and X is halogen, preferably chloride. If each of the three R groups is designated $R_1$, $R_2$ and $R_3$, respectively, the following possibilities exist in certain embodiments: each of $R_1$-$R_3$ can be lower alkyl optionally interrupted with nitrogen or oxygen or substituted with aryl; $R_1$ and $R_2$ can form a ring with $R_3$ being as previously described for $R_1$; $R_2$ and $R_3$ can either be hydrogen with $R_1$ being as previously described; or $R_1$, $R_2$ and $R_3$ can form a bicyclic ring. Most preferably, these groups are methyl or ethyl groups. If desired the di- and tri-alkyl species can be used. One or two of the R groups can be aryl, but this is not preferred. The alkyl groups, and aryl, if present, can be substituted with other groups, such as a halogen. Phenyl and benzyl are representative examples of possible aryl groups to select. However, such further substitution may undesirably increase the viscosity of the melt. Therefore, it is highly desirable that the alkyl groups, and aryl, if present, be comprised of carbon and hydrogen groups, exclusively. Such short chains are preferred because they form the least viscous or the most conductive melts. Mixtures of these alkyl-containing amine hydrohalide salts can be used.

The most preferred alkyl containing amine hydrohalide salt are those compounds where the R groups are either hydrogen or an alkyl group having 1 to 4 carbon atoms, and the hydrohalide is hydrogen chloride, an example of which is trimethylamine hydrochloride.

Figure 2:
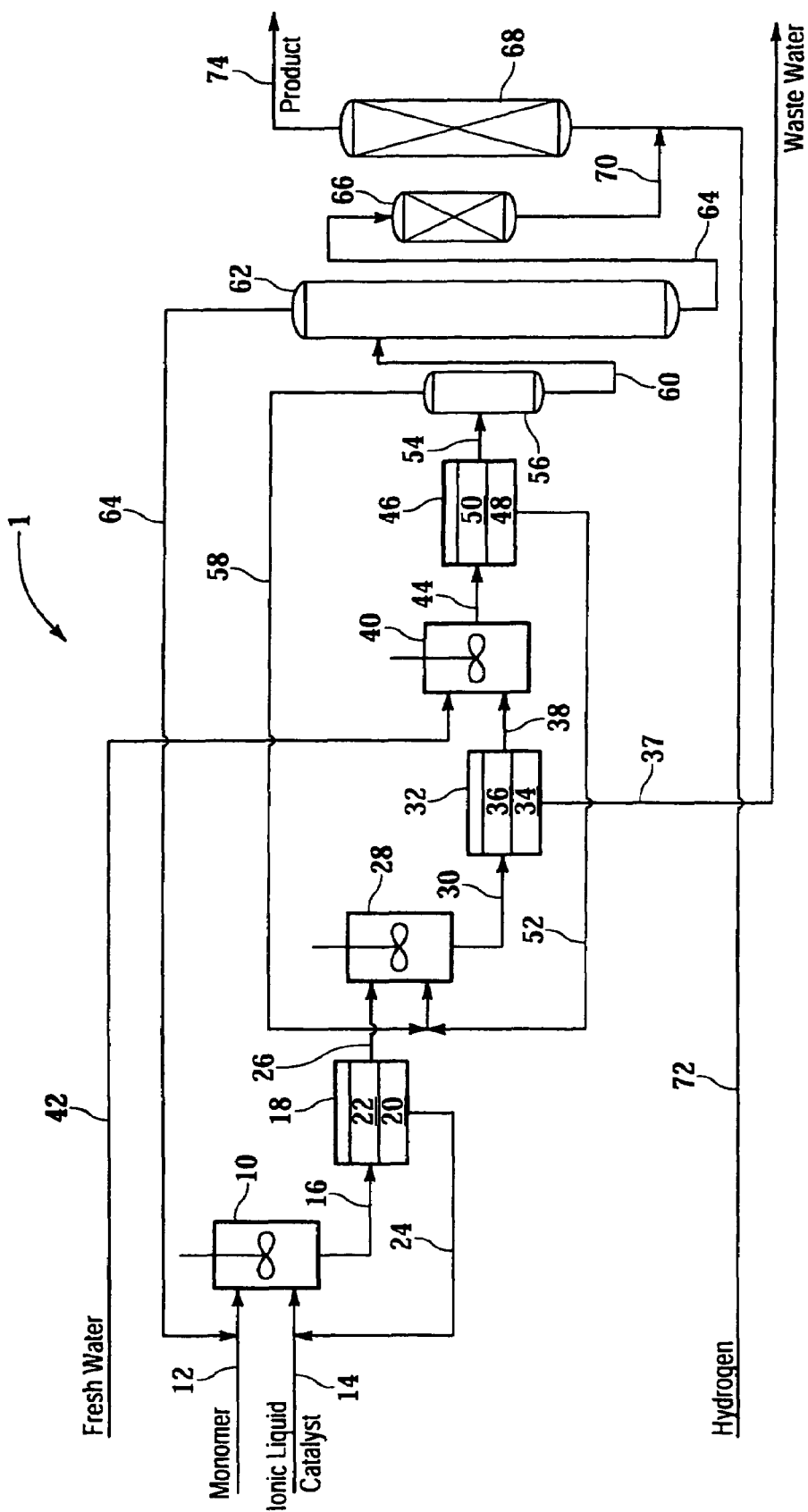
FIG. 2 is a process flow schematic of one embodiment of the process for manufacturing a polyalphaolefin product which also depicts further steps of product separation and hydrogenation of a separated polyalphaolefin product.

Now referring to FIG. 2 wherein is represented production process 1 for manufacturing a hydrogenated polyalphaolefin product. Monomer feed and the recycled monomer and dimer, which is more fully described below, are introduced or charged to continuous stirred tank reaction (CSTR) 10 by way of conduit 12. Makeup ionic liquid catalyst and recycled ionic liquid catalyst feed, which is more fully described below, are introduced or charged to CSTR 10 by way of conduit 14. The monomer and ionic liquid catalyst feeds are simultaneously introduced into the CSTR 10 while the reactor effluent from CSTR 10 is simultaneously with the introduction of the feeds withdrawn from CSTR 10 through conduit 16.

The reactor effluent is passed from CSTR 10 through conduit 16 to first phase separator 18 which provides means for separating the reactor effluent into an ionic liquid catalyst phase 20 and a hydrocarbon or polyalphaolefin-containing phase 22. The separated ionic liquid catalyst phase 20 is recycled by way of conduit 24 and combined with the makeup ionic liquid catalyst passing through conduit 14 and thereby is introduced into CSTR 10.

The polyalphaolefin-containing phase 22 passes from phase separator 18 through conduit 26 to deactivation vessel 28 which provides means for contacting any remaining ionic liquid catalyst mixed with the polyalphaolefin-containing phase with water so as to deactivate the ionic liquid catalyst. The mixture of polyalphaolefin-containing phase, water and deactivated ionic liquid catalyst passes from deactivation vessel 28 through conduit 30 to second phase separator 32 which provides means for separating the waste water and catalyst phases 34 and polyalphaolefin containing phase 36. The waste water phase passes from second phase separator 32 by way of conduit 37.

The polyalphaolefin-containing phase 36 passes from second phase separator 32 through conduit 38 to water wash vessel 40 which provides means for contacting the polyalphaolefin-containing phase 36 with fresh water. The fresh water is charged to or introduced into water wash vessel 40 through conduit 42. The water and polyalphaolefin-containing phases pass from water wash vessel 40 through conduit 44 to third phase separator 46 which provides means for separating the water and the polyalphaolefin-containing phase introduced therein from water wash vessel 40 into a water phase 48 and polyalphaolefin-containing phase 50. The water phase 48 can be recycled and introduced into deactivation vessel 28 through conduit 52 thereby providing the deactivation wash water for use in the deactivation vessel 28.

The polyalphaolefin-containing phase 50 passes from third phase separator 46 through conduit 54 to water separation vessel 56, which provides means for separating water from the polyalphaolefin-containing phase 50, preferably by flash separation, to provide a flash water stream and a polyalphaolefin-containing phase having a low water concentration. The flash water stream can pass from water separation vessel 56 and recycled to deactivation vessel 28 through conduit 58, or alternatively, the flash water stream can be disposed of as waste water via conduit 37. The polyalphaolefin-containing phase having a low water concentration passes from water separation vessel 56 through conduit 60 and is charged to separation vessel 62, which is preferably an evaporator. Separation vessel 62 provides means for separating the polyaolefin-containing phase having a low water concentration into a first stream comprising monomer and, optionally, dimer, and a second stream comprising a polyalphaolefin product The first stream passes from separation vessel 62 by way of conduit 64 and is recycled to conduit 12 wherein it is mixed with the monomer feed and charged to CSTR 10.

The second stream passes from separation vessel 62 through conduit 64 to guard vessel 66, which defines a zone preferably containing alumina and provides means for removing chlorine and other possible contaminants from the second stream prior to charging it to hydrogenation reactor 68. The effluent from guard vessel 66 passes through conduit 70 to hydrogenation reactor 68. Hydrogenation reactor 68 provides means for reacting the polyalphaolefin product in the second stream to provide a hydrogenated polyalphaolefin product of which a substantial portion of the carbon-carbon double bonds are saturated with hydrogen. Hydrogen is introduced by way of conduit 72 into conduit 70 and mixed with the second stream prior to charging the thus-mixed hydrogen and second stream into hydrogenation reactor 68. The hydrogenated polyalphaolefin product passes from hydrogenation reactor 68 by way of conduit 74.

The following examples of the invention are presented merely for the purpose of illustration and are not intended to limit in any manner the scope of the invention.

EXAMPLES 1-3

Batch Oligomerization of 1-Dodecene

The following Examples 1-3 illustrate the effect of the ionic liquid catalyst concentration on certain of the physical properties of the oligomer reaction product resulting from the batch oligomerization of 1-dodecene.

Example 1

400 g of molecular sieve-dried 1-dodecene was added to a three-necked round-bottom flask under a nitrogen purge and heated to 50° C. An addition funnel containing 4.1 g of catalyst (2:1 molar ratio $AlCl_3$:TMA·HCl) was attached to the round-bottom flask. The system was purged with nitrogen and the catalyst was slowly added to the 1-dodecene. The nitrogen purge was continued through the entire reaction. The temperature was controlled with an ice bath and an exotherm (maximum temperature 129° C.) was observed. Samples were pulled every 15 minutes for one hour, neutralized with dilute KOH to quench the catalyst, and filtered through alumina to remove water. Table 1 summarizes the gel permeation chromatography (GPC) results, including the oligomer distribution, weight average molecular weight ($M_w$) and polydispersity index (D) of the sampled product.

TABLE 1

| Product | Units | Example 1a 15 Min. Sample | Example 1b 30 Min. Sample | Example 1c 45 Min. Sample | Example 1d 60 Min. Sample |
|---|---|---|---|---|---|
| Monomer | Weight % | 35.9 | 36.7 | 35.3 | 34.6 |
| Dimer | Weight % | 11.2 | 10.5 | 10.3 | 10.4 |
| Trimer | Weight % | 19.7 | 20.0 | 19.9 | 19.9 |
| Tetramer | Weight % | 10.3 | 10.5 | 10.6 | 10.7 |
| Pentamer+ | Weight % | 22.8 | 22.4 | 23.9 | 24.4 |
| Mw | | 497 | 490 | 506 | 514 |
| D | | 1.63 | 1.60 | 1.62 | 1.63 |

After a total reaction time of one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 9.67 cSt, a viscosity index of 132, and a pour point of −42° C.

Example 2

The conditions of Example 1 were repeated except that 22.1 g of catalyst were used and the initial reaction temperature was 35° C. The analyses of the samples taken during the reaction are presented in Table 2.

TABLE 2

| Product | Units | Example 2a 15 Min. Sample | Example 2b 30 Min. Sample | Example 2c 45 Min. Sample | Example 2d 60 Min. Sample |
|---|---|---|---|---|---|
| Monomer | Weight % | 50.3 | 47.5 | 46.2 | 41.0 |
| Dimer | Weight % | 1.8 | 1.9 | 1.9 | 2.0 |
| Trimer | Weight % | 5.9 | 6.1 | 6.1 | 6.2 |
| Tetramer | Weight % | 5.1 | 5.5 | 5.4 | 5.6 |
| Pentamer+ | Weight % | 37.0 | 39.1 | 40.4 | 45.3 |
| Mw | | 625 | 648 | 676 | 744 |
| D | | 2.21 | 2.20 | 2.25 | 2.28 |

After one hour, the catalyst was removed from the reaction vessel with a syringe. Dilute KOH was then added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 17.7 cSt, a viscosity index of 154, and a pour point of −36° C.

Example 3

The conditions of Example 1 were repeated except that 40.1 g of catalyst were used and the initial reaction temperature was 20° C. The analyses of the samples taken during the reaction are presented in Table 3.

TABLE 3

| Product | Units | Example 3a 15 Min. Sample | Example 3b 30 Min. Sample | Example 3c 45 Min. Sample | Example 3d 60 Min. Sample |
|---|---|---|---|---|---|
| Monomer | Weight % | 18.8 | 11.1 | 8.1 | 3.3 |
| Dimer | Weight % | 1.7 | 1.7 | 1.3 | 2.0 |
| Trimer | Weight % | 5.8 | 5.8 | 5.4 | 5.8 |
| Tetramer | Weight % | 5.9 | 6.1 | 5.8 | 6.6 |
| Pentamer+ | Weight % | 68.0 | 75.4 | 79.4 | 82.4 |
| Mw | | 1133 | 1257 | 1318 | 1346 |
| D | | 2.12 | 1.84 | 1.70 | 1.45 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 26.6 cSt, a viscosity index of 172, and a pour point of −30° C.

Examples 1-3 demonstrate that, for the batch oligomerization of 1-dodecene, both the values for the kinematic viscosity and viscosity index of the end-product unexpectedly increases with an increase in the ionic liquid catalyst concentration. The pour point temperature of the end-product also increases with increasing catalyst concentration.

EXAMPLES 4-6

Batch Oligomerization of 1-Decene

The following Examples 4-6 illustrate the effect of ionic liquid catalyst concentration on certain of the physical properties of the oligomerization reaction product resulting from the batch oligomerization of 1-decene.

Example 4

The conditions of Example 1 were repeated except that 4.0 g of catalyst were used, 1-decene was substituted for 1-dodecene, and the initial reaction temperature was 50° C. The analyses of the samples taken during the reaction are presented in Table 4.

TABLE 4

| Product | Units | Example 4a 15 Min. Sample | Example 4b 30 Min. Sample | Example 4c 45 Min. Sample | Example 4d 60 Min. Sample |
|---|---|---|---|---|---|
| Monomer | Weight % | | | | 52.0 |
| Dimer | Weight % | | | | 6.5 |
| Trimer | Weight % | | | | 8.4 |
| Tetramer | Weight % | | | | 13.6 |
| Petamer | Weight % | | | | 4.6 |
| Hexamer | Weight % | | | | 14.9 |
| Mw | | 256 | 256 | 253 | 263 |
| D | | 1.36 | 1.36 | 1.36 | 1.37 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 8.55 cSt, a viscosity index of 137, and a pour point of −57° C.

Example 5

The conditions of Example 4 were repeated except that 22.1 g of catalyst were used and the initial reaction temperature was 35° C. The analyses of the samples taken during the reaction are presented in Table 5.

TABLE 5

| Product | Units | Example 5a 15 Min. Sample | Example 5b 30 Min. Sample | Example 5c 45 Min. Sample | Example 5d 60 Min. Sample |
|---|---|---|---|---|---|
| Monomer | Weight % | | | | 32.5 |
| Dimer | Weight % | | | | 4.0 |
| Trimer | Weight % | | | | 12.0 |
| Tetramer | Weight % | | | | 8.8 |
| Pentamer | Weight % | | | | 10.0 |
| Hexamer+ | Weight % | | | | 32.7 |
| Mw | | 400 | 369 | 368 | 464 |
| D | | 1.71 | 1.70 | 1.70 | 1.73 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity of 14.27 cSt, a viscosity index of 146, and a pour point of −51° C.

Example 6

The conditions of Example 4 were repeated except that 40 g of catalyst were used and the initial reaction temperature was 20° C. The analyses of the samples taken during the reaction are presented in Table 6.

TABLE 6

| Product | Units | Example 6a 15 Min. Sample | Example 6b 30 Min. Sample | Example 6c 45 Min. Sample | Example 6d 60 Min. Sample |
|---|---|---|---|---|---|
| Monomer | Weight % | | | | 13.1 |
| Dimer | Weight % | | | | 6.6 |

TABLE 6-continued

| Product | Units | Example 6a 15 Min. Sample | Example 6b 30 Min. Sample | Example 6c 45 Min. Sample | Example 6d 60 Min. Sample |
|---|---|---|---|---|---|
| Trimer | Weight % | | | | 15.5 |
| Tetramer | Weight % | | | | 15.6 |
| Pentamer | Weight % | | | | 14.6 |
| Hexamer+ | Weight % | | | | 34.5 |
| Mw | | 370 | 368 | 367 | 652 |
| D | | 1.80 | 1.82 | 1.81 | 1.58 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 18.31 cSt, a viscosity index of 153, and a pour point −48° C.

Examples 4-6 demonstrate that for the batch oligomerization of 1-decene, both the values for the kinematic viscosity and viscosity index of the end-product unexpectedly increases with an increase in the ionic liquid catalyst concentration. The pour point temperature of the end-product also increases with increasing catalyst concentration.

EXAMPLES 7-9

Continuous Oligomerization of 1-Dodecene

The following Examples 7-9 illustrate the novel continuous process for the manufacture of a high viscosity polyalphaolefin product from a 1-dodecene feedstock using an ionic liquid catalyst. These Examples further illustrate the effect of ionic liquid catalyst concentration on certain of the physical properties of the oligomer reaction product resulting from the continuous process for the oligomerization of 1-dodecene.

Example 7

In a continuous process, 1-dodecene was fed at a rate of 50 lbs/hr along with a catalyst feed (1.65:1 molar ratio $AlCl_3$:TMA·HCl) of 0.5 lbs/hr into a 2-gallon stirred-tank reactor with an external cooling loop including a pump and heat exchanger. The cooling loop had a 10 gpm circulation rate. The reactor stirrer was set at a tip speed of 1150 ft/min. The reaction section had a 30-minute residence time and temperature was maintained at 95° F. with a pressure of 15 psig. The reactor effluent was quenched with water to deactivate the active catalyst. Oligomer distribution data, molecular weight average ($M_w$) and polydispersity (D) were determined using gel permeation chromatography (GPC) on the resulting reaction product. A sample of the resulting product was distilled to contain less than 1% monomer and hydrogenated in the laboratory. Certain of the physical properties of the distilled and hydrogenated polyalphaolefin product were determined. The properties of the polyalphaolefin product of this Example 7 and of the polyalphaolefin product of the following Examples 8-10 are presented in Table 7 below.

TABLE 7

| Product | Units | Example 7 | Example 8 | Example 9 | Example 10 |
|---|---|---|---|---|---|
| Monomer | Weight % | 44.3 | 0.3 | 47.7 | 0.8 |
| Dimer | Weight % | 1.0 | 0.4 | 0.6 | 0.7 |
| Trimer | Weight % | 3.7 | 1.8 | 2.5 | 2.1 |
| Tetramer | Weight % | 3.8 | 3.1 | 2.7 | 3.2 |
| Pentamer | Weight % | 5.5 | 4.9 | 4.1 | 4.7 |
| Hexamer | Weight % | 5.0 | 5.3 | 4.0 | 5.4 |
| Heptamer+ | Weight % | 36.7 | 84.3 | 38.5 | 83.1 |
| Mw | | 851 | 1796 | 748 | 1649 |
| D | | 2.70 | 1.67 | 2.88 | 1.41 |
| 100° C. Viscosity | cSt | 18.6 | 32.3 | | 22.1 |
| Viscosity Index | | 156 | 157 | | 151 |
| Pour Point | ° C. | −36 | −36 | | −45 |

Example 8

The conditions for Example 7 were repeated with the exception of the catalyst feed rate which was 4 lb/hr. The polyalphaolefin product was obtained as described in Example 7, the properties of which are presented in Table 7.

Example 9

The conditions for Example 7 were repeated with the exception of the reaction temperature which was 70° F. The polyalphaolefin product was obtained as described in Example 7, the properties of which are presented in Table 7.

Examples 7-9 demonstrate that a high viscosity polyalphaolefin product having desirable physical properties can be manufactured using a continuous process for the ionic liquid catalyzed oligomerization of an alpha olefin monomer. The Examples also demonstrate that the values for the kinematic viscosity and viscosity index of the end-product from the continuous oligomerization of 1-decene increase with increasing concentration of ionic liquid catalyst. An oligomer end-product having a significantly high kinematic viscosity is obtainable from the continuous process.

EXAMPLE 10

Continuous Oligomerization of 1-Decene

This Example 10 illustrates the novel continuous process for the manufacture of a high viscosity polyalphaolefin product from a 1-decene feedstock using an ionic liquid catalyst.

Example 10

The conditions for Example 7 were repeated with the exception of the catalyst feed rate which was 1.3 lb/hr and the feed was 1-decene. The resulting product was then processed in batch operation to flash out the monomer and to hydrogenate the end-product. Certain of the physical properties of the polyalphaolefin product were determined. These physical properties are presented in Table 7.

Example 10 further demonstrates that a high viscosity polyalphaolefin product having desirable physical properties can be manufactured using a continuous process for the ionic liquid catalyzed oligomerization of an alpha olefin monomer. An oligomer end-product having a high kinematic viscosity is obtainable from the continuous process.

EXAMPLES 11-12

Controlling Water in Reaction

Example 11

In a continuous process, 1-decene was fed at a rate of 2786 g/hr along with a catalyst feed (1.65:1 molar ratio $AlCl_3$:TMA·HCl) of 59.3 g/hr into a 1-gallon stirred-tank reactor with an internal cooling coil and a recirculation loop with a mixing pump. The reactor stirrer speed was set at 660 rpm. The reaction section had a 31-minute residence time and temperature was maintained at 40° C. with a nitrogen pressure of 31 psig. The reactor effluent was quenched with water to deactivate the active catalyst. The resulting 1-decene conversion was 36.2%.

Example 12

This example illustrates how moisture in the nitrogen affects 1-decene conversion. In a continuous process, 1-decene was fed at a rate of 2928 g/hr along with a catalyst feed (1.65:1 molar ratio $AlCl_3$:TMA·HCl) of 51.1 g/hr into a stirred-tank reactor. The reactor configuration was identical to that described in Example 11, except the nitrogen headspace gas in the reactor was sparged through a water tank at a rate of 0.5 SCFH. The reactor stirrer speed was set at 400 rpm. The reaction section had a 36-minute residence time and temperature was maintained at 40° C. The resulting 1-decene conversion was 68.3%.

Although the invention has been described in detail and with preferred embodiments, it is to be understood that modifications and variations may be resorted to, without departing from the spirit and scope of the invention. Such modifications and variations are considered to be within the provisions and scope of the appended claims.

That which is claimed is:

1. A method comprising:
    simultaneously introducing into a reaction zone a monomer feed and an ionic liquid catalyst, the monomer feed comprising greater than 50 weight percent alpha olefins; and
    simultaneously with introducing said monomer feed and said ionic liquid catalyst into said reaction zone, withdrawing from said reaction zone a reactor effluent comprising a polyalphaolefin product;
    wherein the weight ratio of said ionic liquid catalyst to said monomer feed introduced into said reaction zone is in the range upwardly to about 1:1; and
    wherein said ionic liquid catalyst is formed by the combination of a metal halide and an alkyl-containing amine hydrohalide salt.

2. A method as recited in claim 1 wherein the residence time is in the range upwardly to about 300 minutes, the reaction pressure is in the range of from below atmospheric upwardly to about 250 psia, and the reaction temperature is in the range of from about 35° F. to about 200° F.

3. A method as recited in claim 2 wherein the kinematic viscosity at 100° C. of said polyalphaolefin product is in the range exceeding about 8 cSt.

4. A method as recited in claim 3 wherein said monomer feed comprises at least one alpha olefin having from 4 to 14 carbon atoms.

5. A method of continuously producing a polyalphaolefin product, said method comprises the steps of:
    introducing a monomer feed into a continuous stirred reactor;
    simultaneously with introducing said monomer feed into said continuous stirred reactor, introducing a catalyst consisting essentially of an ionic liquid at a specified rate into said continuous stirred reactor;
    while introducing said monomer feed into said continuous stirred reactor, withdrawing from said continuous stirred reactor a single reactor effluent, the single reactor effluent comprising said polyalphaolefin product having a desired viscosity; and
    controlling said specified rate of introduction of said ionic liquid catalyst so as to provide said desired viscosity;
    wherein said specified rate of introduction of said ionic liquid catalyst into said continuous stirred reactor is such that the weight ratio of said ionic liquid catalyst to said monomer feed is in the range upwardly to about 1:1; and
    wherein said desired viscosity is a kinematic viscosity at 100° C. exceeding about 8 cSt.

6. A method as recited in claim 5 wherein said ionic liquid catalyst is formed by the combination of a metal halide and an alkyl-containing amine hydrohalide salt.

7. A method as recited in claim 6 wherein the residence time is in the range upwardly to about 300 minutes, the reaction pressure is in the range of from below atmospheric upwardly to about 250 psia, and the reaction temperature is in the range of from about 35° F. to about 200° F.

8. A method as recited in claim 7 wherein said monomer feed comprises at least one alpha olefin having from 4 to 14 carbon atoms and wherein the concentration of alpha olefin in said monomer feed is at least about 50 weight percent of said monomer feed.

9. A method of manufacturing a polyalphaolefin product, said method comprises the steps of:
    introducing a monomer feed comprising greater than 50 weight percent alpha olefins and a catalyst feed consisting essentially of an ionic liquid into a continuous stirred reactor;
    simultaneous with introducing the monomer feed, withdrawing from said continuous stirred reactor a single reactor effluent, the single reactor effluent comprising said polyalphaolefin product, wherein said reactor effluent further comprises said ionic liquid catalyst, said alpha olefin and, optionally, a dimer compound;
    separating at least a portion of said ionic liquid catalyst from said reactor effluent to thereby provide an ionic liquid catalyst phase and a polyalphaolefin-containing phase;
    separating said polyalphaolefin-containing phase into a first separated product comprising said alpha olefin and, optionally, said dimer, and a second separated product comprising said polyalphaolefin product; and
    hydrogenating said second separated product to provide a hydrogenated polyalphaolefin product.

10. The method as recited in claim 1 further comprising controlling the amount of water present in the reaction zone to maintain a conversion reaction of the monomer and avoid deactivating the catalyst.

11. The method as recited in claim 5 further comprising controlling the amount of water present in the reaction zone to maintain a conversion reaction of the monomer and avoid deactivating the catalyst.

12. The method as recited in claim 9 further comprising controlling the amount of water present in the reaction zone to maintain a conversion reaction of the monomer and avoid deactivating the catalyst.

13. The method as recited in claim 1 wherein the ionic liquid catalyst is formed from a group VIII, IB, IIB, or IIIA metal halide.

14. The method as recited in claim 1 wherein the ionic liquid catalyst is formed from a group IB, IIB, or IIIA metal halide.

15. The method as recited in claim 1 wherein the ionic liquid catalyst is formed from an aluminum halide.

16. The method as recited in claim 5 wherein the ionic liquid is formed from a group VIII, IB, IIB, or IIIA metal halide.

17. The method as recited in claim 5 wherein the ionic liquid is formed from a group IB, IIB, or IIIA metal halide.

18. The method as recited in claim 5 wherein the ionic liquid is formed from an aluminum halide.

19. The method as recited in claim 9 wherein the ionic liquid is formed from a group VIII, IB, IIB, or IIIA metal halide.

20. The method as recited in claim 9 wherein the ionic liquid is formed from a group IB, IIB, or IIIA metal halide.

21. The method as recited in claim 9 wherein the ionic liquid is formed from an aluminum halide.

\* \* \* \* \*